(12) United States Patent
Morel et al.

(10) Patent No.: US 12,736,181 B2
(45) Date of Patent: Sep. 15, 2026

(54) LEAKTIGHT AND THERMALLY INSULATING VESSEL, AND ASSOCIATED METHOD FOR PLACING UNDER VACUUM

(71) Applicant: GAZTRANSPORT ET TECHNIGAZ, Saint-Remy-les-Chevreuse (FR)

(72) Inventors: Benoît Morel, Saint-Remy-les-Chevreuse (FR); Guillaume De Combarieu, Saint-Remy-les-Chevreuse (FR); Guillaume Salmon Legagneur, Saint-Remy-les-Chevreuse (FR)

(73) Assignee: GAZTRANSPORT ET TECHNIGAZ, Saint-Remy-les-Chevreuse (FR)

( * ) Notice: Subject to any disclaimer, the term of this patent is extended or adjusted under 35 U.S.C. 154(b) by 72 days.

(21) Appl. No.: 18/855,844

(22) PCT Filed: Apr. 13, 2023

(86) PCT No.: PCT/EP2023/059702
§ 371 (c)(1),
(2) Date: Oct. 10, 2024

(87) PCT Pub. No.: WO2023/198843
PCT Pub. Date: Oct. 19, 2023

(65) Prior Publication Data

US 2025/0251085 A1 Aug. 7, 2025

(30) Foreign Application Priority Data

Apr. 15, 2022 (FR) .................................. FR2203554

(51) Int. Cl.
*F17C 1/12* (2006.01)
*C01B 32/50* (2017.01)
(Continued)

(52) U.S. Cl.
CPC .............. *F17C 3/027* (2013.01); *C01B 32/50* (2017.08); *C07C 21/18* (2013.01); *F17C 3/08* (2013.01);
(Continued)

(58) Field of Classification Search
CPC ...... F17C 5/04; F17C 5/06; F17C 5/02; F17C 3/08; F17C 1/12; F17C 3/027;
(Continued)

(56) References Cited

U.S. PATENT DOCUMENTS 2,677,938 A * 5/1954 Loveday ............... F17C 13/083 220/592.27
3,695,050 A 10/1972 Bancroft
(Continued)

FOREIGN PATENT DOCUMENTS

EP 3181986 A1 6/2017
WO WO2015078972 A1 6/2015
(Continued)

OTHER PUBLICATIONS

International Search Report and Written Opinion for International Application No. PCT/EP2023/059702, Mailed on Jul. 5, 2023—with translations.
(Continued)

*Primary Examiner* — Stephen J Castellano
(74) *Attorney, Agent, or Firm* — Notaro, Michalos & Zaccaria P.C.

(57) ABSTRACT

A method for placing an intermediate space in a leaktight and thermally insulating vessel under vacuum. The intermediate space (30) comprises a gas phase, the gas phase consisting of one or more main chemical species and optionally one or more residual chemical species. The main chemical species has a saturation vapor pressure, at any temperature below 126 K, that is less than the saturation
(Continued)

vapor pressure of nitrogen at said temperature below 126 K. The pressure in the intermediate space is at an absolute pressure below a pressure threshold, the pressure threshold being less than the triple point of said or each main chemical species. The residual chemical species is at a partial pressure of less than 0.1 kPa.

28 Claims, 4 Drawing Sheets

(51) Int. Cl.
*C07C 21/18* (2006.01)
*F17C 3/02* (2006.01)
*F17C 3/08* (2006.01)

(52) U.S. Cl.
CPC ................ *F17C 2223/0153* (2013.01); *F17C 2270/0105* (2013.01)

(58) Field of Classification Search
CPC ........... F17C 2223/0153; F17C 13/002; F17C 2203/0391; F17C 2203/0375
See application file for complete search history.

(56) References Cited

U.S. PATENT DOCUMENTS 5,408,832 A * 4/1995 Boffito ................. F16L 59/065 62/51.1
6,119,465 A 9/2000 Mullens et al.

FOREIGN PATENT DOCUMENTS

WO WO2015124536 A2 8/2015
WO WO2015132307 A1 9/2015

OTHER PUBLICATIONS

Sass; J. P. et al., "Glass Bubbles Insulation for Liquid Hydrogen Storage Tanks", Glass bubbles insulation for liquid hydrogen storage tanks, AIP Conf. Proc. 1218, 772-779 (2010), https://doi.org/10.1063/1.3422430 American Institute of Phyics, Jun. 28, 2009-Jul. 2, 2009, Published Apr. 23, 2010.

* cited by examiner

[Fig. 1]
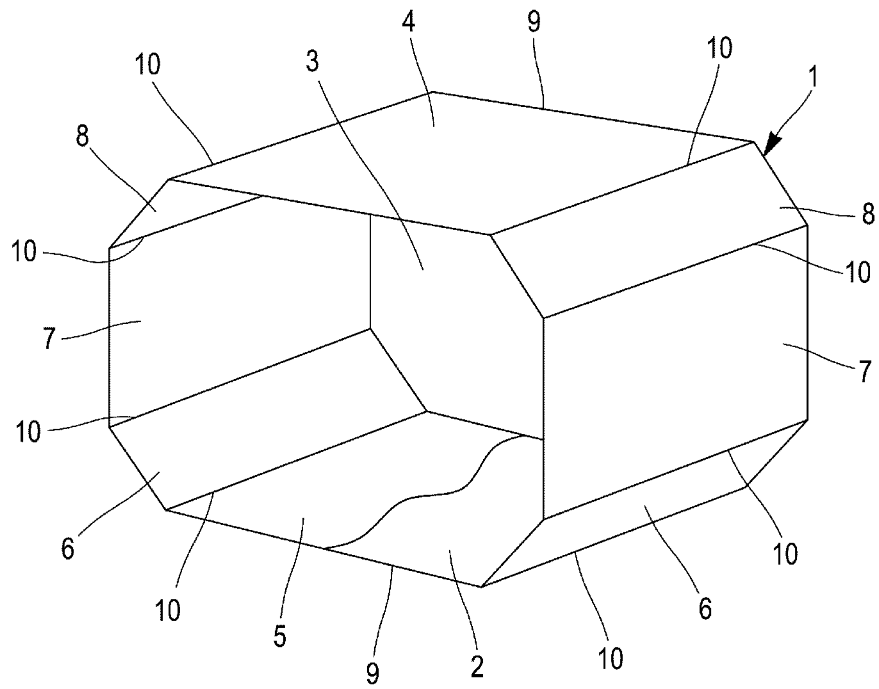
[Fig. 2]
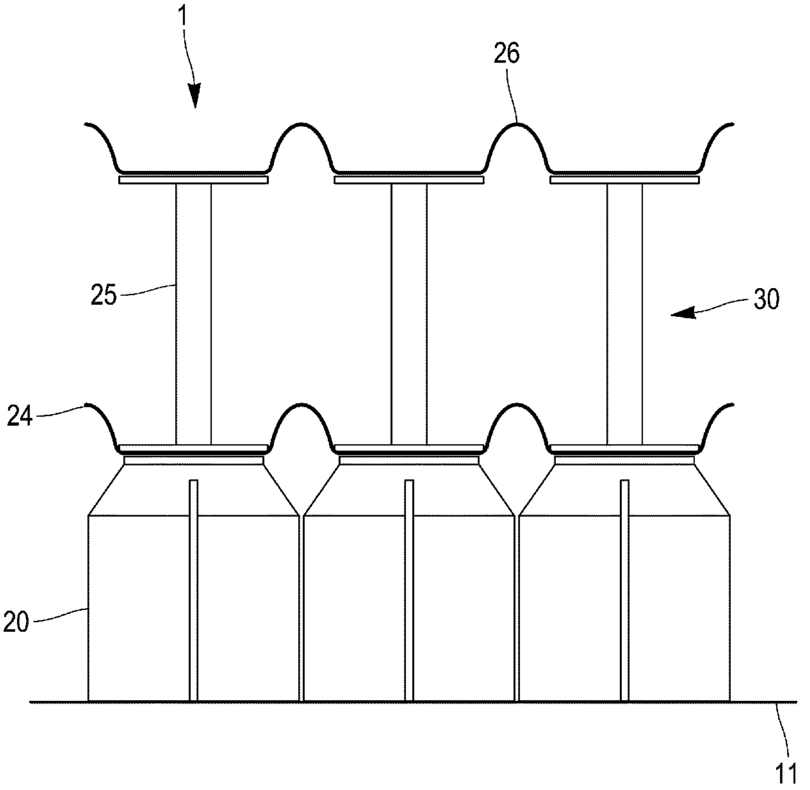

[Fig. 3]

[Fig. 4]
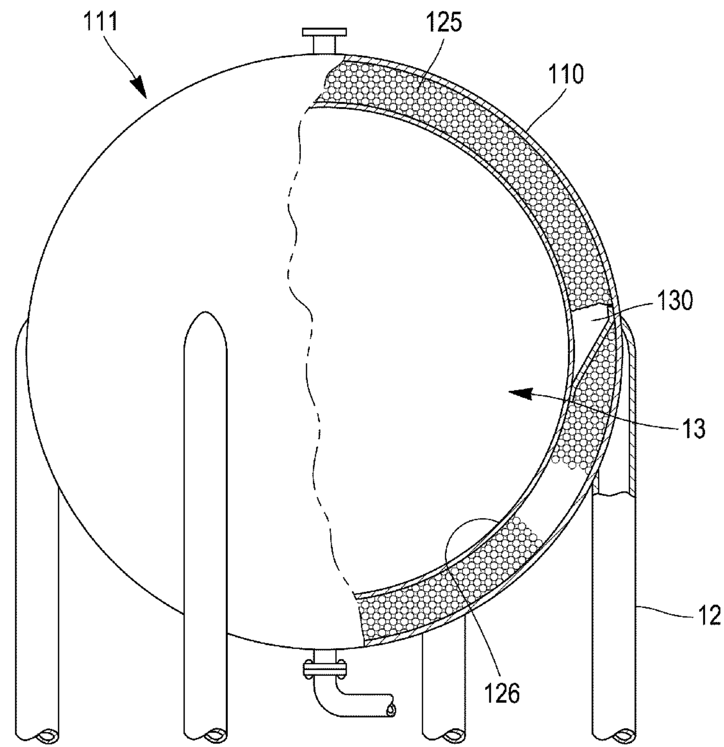
[Fig. 5]
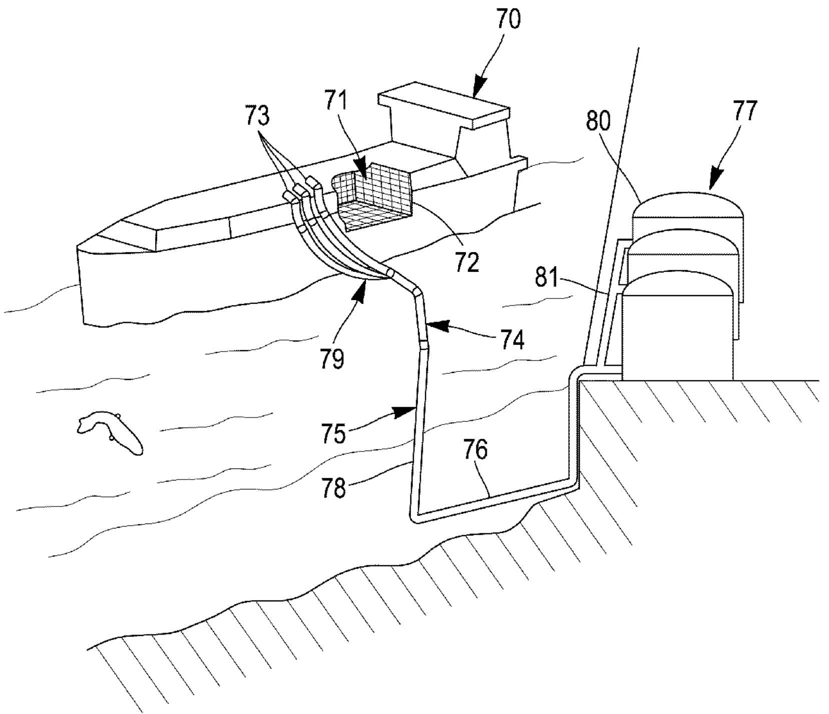

[Fig. 6]
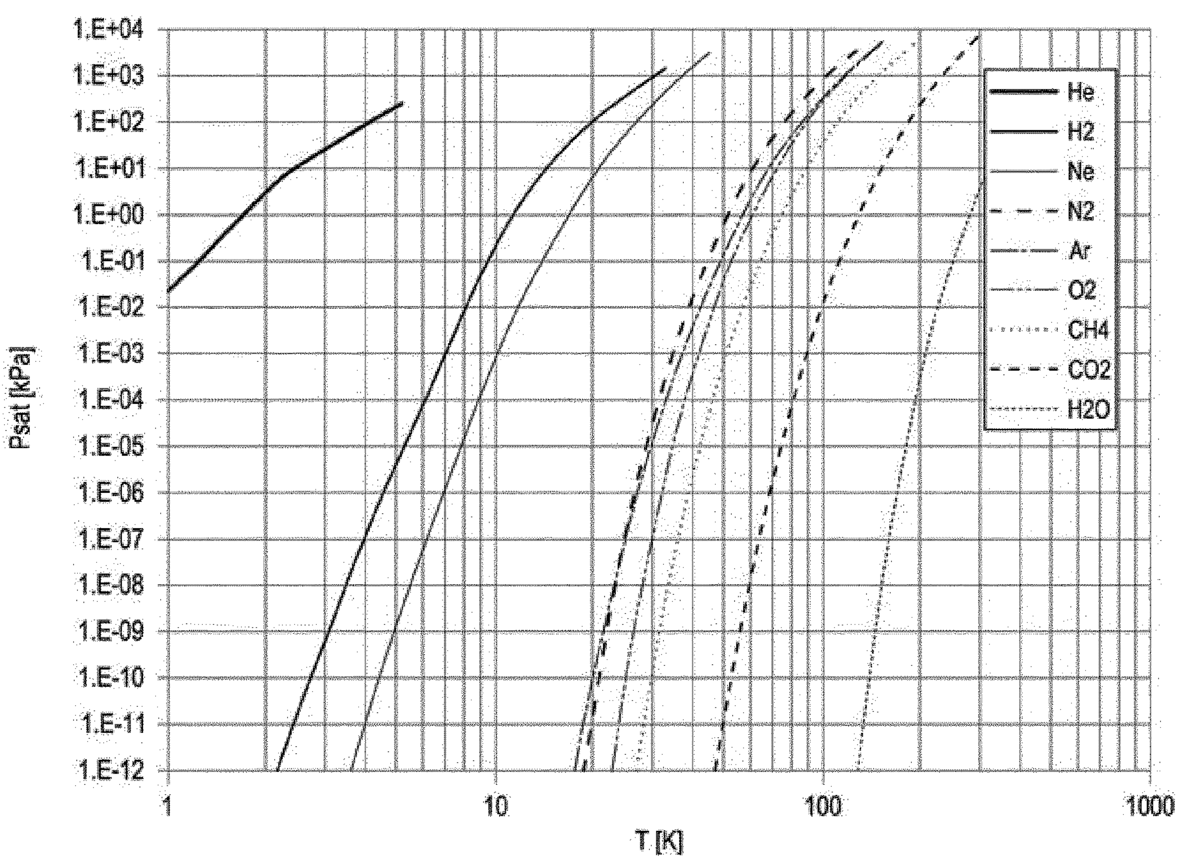

LEAKTIGHT AND THERMALLY INSULATING VESSEL, AND ASSOCIATED METHOD FOR PLACING UNDER VACUUM

TECHNICAL FIELD

The invention relates to the field of the sealed and thermally insulating tanks used for the storage and/or transportation of liquefied gas at low temperature, such as a tank for transporting liquid hydrogen, which is at approximately −253° C. at atmospheric pressure but which can also be stored under a higher pressure. These tanks can be installed at a fixed station or any onshore or floating vehicle.

TECHNOLOGICAL BACKGROUND

Onshore self-supporting tanks are known for the storage and/or transportation of liquefied gas at atmospheric pressure.

Also known are membrane tanks for storing and/or transporting liquefied natural gas at atmospheric pressure. Such a tank comprises, for example, a tank wall that has, in succession, in the thicknesswise direction, from the inside to the outside of the tank, a primary sealing membrane intended to be in contact with the liquefied natural gas, a primary thermally insulating barrier, a secondary sealing membrane, a secondary thermally insulating barrier and a bearing structure defining the general form of the tank.

The primary and secondary sealing membranes delimit between them a primary space which contains the primary insulating barrier.

In order to keep the gas in liquid form inside the tank, it is important for the tank to have excellent thermal insulation properties. Indeed, such a tank must limit as far as possible the heating up of the liquefied gas contained inside the tank and therefore limit the thermal conduction to the outside of the tank which could damage elements sensitive to the low temperatures.

It is known practice, for example from the document Glass bubbles insulation for liquid hydrogen storage tanks, J. P. Sass, W. W. St. Cyr, T. M. Barrett, R. G. Baumgartner, J. W. Lott, and J. E. Fesmirel, Jun. 30, 2009, to reduce the pressure of the intermediate space of a self-supporting spherical tank in order to improve the thermal insulation properties of the tank.

Nevertheless, the evacuation method for evacuating such an intermediate space by means of vacuum pumps in the tank is a lengthy and energy-intensive process.

In other words, it is difficult to extract all of the air initially present in the space. Thus, it is difficult to extract nitrogen and oxygen which are the main constituents of air.

SUMMARY

Certain aspects of the invention start from the observation that, when the tank is being cooled, the chemical species such as the oxygen and the nitrogen initially in gaseous phase can condense into liquid phase and possibly, in a second stage, solidify into solid phase if the pressure and the temperature decrease sufficiently. Thus, the nitrogen for example can easily spread out in the primary space in liquid phase and then solidify.

This phenomenon leads to damage to the tank, with in particular the reduction of the thermal insulation properties of the tank through the formation of liquid or ice spread out in the thickness of the primary space, thus forming thermal bridges.

One idea on which the invention is based is to propose an evacuation method for evacuating an intermediate space in a sealed and thermally insulating tank.

Another idea on which the invention is based is to propose an improved evacuation method for evacuating an intermediate space in a sealed and thermally insulating tank, offering advantages in terms of speed and energy consumption.

Another idea on which the invention is based is to propose an evacuation method for evacuating an intermediate space in a sealed and thermally insulating tank that is more economical in terms of energy and less costly than the known evacuation methods.

Another idea on which the invention is based is to propose a sealed and thermally insulating tank comprising a gaseous phase in an intermediate space exhibiting excellent physicochemical properties.

In particular, an idea on which the invention is based is to propose a gaseous phase in an intermediate space in conditions that allow said gaseous phase, in case of temperature reduction, to condense from a gaseous phase to a solid phase without passing through a liquid phase.

According to one embodiment, the invention provides an evacuation method for evacuating an intermediate space in a sealed and thermally insulating tank, the sealed and thermally insulating tank comprising an outer sealed wall, an inner sealed wall situated at a distance from an inner side of the outer sealed wall and defining an internal space intended to contain the liquefied gas, preferentially hydrogen, and an intermediate space situated between the outer sealed wall and the inner sealed wall, the method comprising the steps of:

- replacing a gaseous phase present in the intermediate space with a replacement gaseous phase at a first temperature, the first temperature being greater than 273 K, the replacement gaseous phase being composed of one or more main chemical species, and possibly one or more residual chemical species, the replacement of the gaseous phase comprising the step of injecting the replacement gaseous phase into the intermediate space at a first pressure, the first pressure in the intermediate space being less than 500 kPa absolute, in which the or each main chemical species is in the gaseous state at the first temperature and at a partial pressure lower than the first pressure, in which the or each main chemical species exhibits a saturating vapour pressure at any temperature lower than 126 K lower than the saturating vapour pressure of nitrogen at said temperature lower than 126 K,
- lowering the pressure in the intermediate space to an absolute pressure lower than a pressure threshold, and
- cooling the tank by injecting a fluid at a second temperature lower than 273 K into the internal space of the tank,
- wherein the pressure threshold is lower than the triple point of said or each main chemical species, to make said or each main chemical species condense into solid phase upon the cooling of the tank, and wherein the or each residual chemical species is at a partial pressure lower than 0.1 kPa.

The gaseous phase initially present comprises, for example, air which is primarily composed of nitrogen and oxygen. It is therefore important to replace this gaseous phase that is initially present in order to prepare the evacuation of the intermediate space. Thus, the or each main chemical species is in the gaseous state before the cooling of the tank and condenses to the solid phase in the form of snow or icicles, when the temperature decreases, without passing through the liquid state. Thus, this condensation would considerably reduce the volume occupied by the main chemical species and therefore the pressure prevailing in the intermediate space. Furthermore, the risk of a chemical species present in the intermediate space condensing into liquid phase and spreading out in the primary space is greatly reduced. The formation of a thermal bridge across the intermediate space is also greatly reduced.

According to embodiments, such an evacuation method can comprise one or more of the following features.

According to one embodiment, the first pressure is lower than 110 kPa absolute. Thus, the pressure forces on the sealed walls are moderate, which allows relatively lightweight constructions, notably in the form of membranes.

According to one embodiment, the pressure threshold is lower than 1 kPa, preferentially lower than 0.1 kPa. Thus, the quantity of material likely to condense during the cooling is relatively small.

According to one embodiment, the saturating vapour pressure at any temperature lower than 126 K of the or each main chemical species is lower than the saturating vapour pressure of nitrogen at the temperature lower than 126 K in a ratio of less than 1/10, preferentially a ratio of less than 1/1000, even more preferentially a ratio of less than 1/10000.

According to one embodiment, the or each residual chemical species is at a partial pressure lower than 10 Pa, preferentially lower than 1 Pa.

Thus, the quantity of residual chemical species present in the space that can potentially condense into liquid phase is very small. By virtue of these features, the thermal insulation capacities of the tank are therefore preserved.

According to one embodiment, the or each main chemical species is chosen from among: carbon dioxide and trans-1,3,3,3-tetrafluoropropene.

According to one embodiment, the replaced gaseous phase comprises carbon dioxide as single main species.

Thus, when the tank is being cooled, the carbon dioxide will condense into solid phase without passing through the liquid phase and form a more or less porous solid phase. Carbon dioxide is a preferred main species which can easily be condensed into solid phase during the cooling of the tank. The phase transition of the carbon dioxide from the gaseous phase to the solid phase leads to an additional reduction of the pressure in the intermediate space. Thus, the thermal insulation properties of the tank are augmented.

According to one embodiment, the replacement of the gaseous phase present in the intermediate space comprises:

- sucking said gaseous phase present in the intermediate space to the outside of the outer sealed wall until the absolute pressure in the intermediate space is lower than a second pressure threshold, wherein the second pressure threshold is lower than 20 kPa, preferentially lower than 10 kPa, even more preferentially lower than 1 kPa, then injecting the replacement gaseous phase into the intermediate space.

According to one embodiment, the steps of suction of the gaseous phrase present in the intermediate space and of injection of the replacement gaseous phase are performed repeatedly.

According to one embodiment, the replacement of the gaseous phase present in the intermediate space simultaneously comprises sucking said gaseous phase present in the intermediate space to the outside of the outer sealed wall and injecting the replacement gaseous phase into the intermediate space, in order to perform a scavenging of the intermediate space with the replacement gaseous phase.

According to one embodiment, the first temperature is higher than 330 K, preferentially higher than 373.15 K. Thus, the water present in the intermediate space at ambient temperature is vaporized and will be able to be discharged easily from this intermediate space.

According to one embodiment, the cooling of the tank is performed by spraying fluid into the internal space of the tank.

According to one embodiment, the cooling of the tank is performed by filling the internal space of the tank via a filling line emerging in a bottom part of the tank.

According to one embodiment, the fluid is liquid hydrogen.

According to one embodiment, the fluid is liquid argon, liquid helium or liquid dinitrogen.

According to one embodiment, the sealed and thermally insulating tank comprises a secondary sealed membrane situated between the outer sealed wall and the inner sealed wall, the intermediate space being formed between the secondary sealed membrane and the inner sealed wall, the inner sealed wall being a primary sealed membrane, wherein the intermediate space comprises support elements extending in the thicknesswise direction to support the primary sealed membrane.

Such support elements can be produced in multiple ways, for example in the form of blocks of insulating material, rigid box sections, pillars, spacer walls, etc.

According to one embodiment, the invention also provides a sealed and thermally insulating tank comprising an outer sealed wall, an inner sealed wall situated at a distance from an inner side of the outer sealed wall and defining an internal space intended to contain the liquefied gas, preferably hydrogen, and an intermediate space situated between the outer sealed wall and the inner sealed wall,

- wherein the intermediate space comprises a gaseous phase,
- the gaseous phase being composed of one or more main chemical species, and possibly one or more residual chemical species,
- wherein the or each main chemical species exhibits a saturating vapour pressure at any temperature lower than 126 K lower than the saturating vapour pressure of nitrogen at said temperature lower than 126 K,
- wherein the gaseous phase in the intermediate space is at an absolute pressure lower than a pressure threshold, said pressure threshold being lower than the triple point of said or each main chemical species, and
- wherein the or each residual chemical species is at a partial pressure lower than 0.1 kPa.

According to one embodiment, the internal space contains liquefied gas, the liquefied gas having a temperature lower than 273 K.

According to one embodiment, the internal space contains liquefied gas, the liquefied gas having a temperature lower than 173 K, preferentially lower than 123 K, for example lower than 50 K.

According to one embodiment, the internal space contains liquid hydrogen.

According to one embodiment, said or each main chemical species is chosen from among: carbon dioxide and trans-1,3,3,3-tetrafluoropropene.

According to one embodiment, the carbon dioxide is the single main species of the gaseous phase.

According to one embodiment, the tank comprises a secondary sealed membrane situated between the outer sealed wall and the inner sealed wall, the intermediate space being formed between the secondary sealed membrane and the inner sealed wall, the inner sealed wall being a primary sealed membrane, wherein the intermediate space comprises a primary thermally insulating barrier supporting the primary sealed membrane.

Such a tank can form part of an onshore storage installation, for example for storing liquid hydrogen, or be installed in a floating, coastal or deep water structure, notably a ship, a floating storage and regassification unit (FSRU), a floating production and storage offshore unit (FPSO), and the like.

According to one embodiment, a ship for transporting a liquefied gas, preferentially for transporting hydrogen, comprises a double-hull and an abovementioned tank disposed in the double-hull.

According to one embodiment, the double-hull comprises an inner hull forming the bearing structure of the tank.

According to one embodiment, the invention also provides a transfer system for liquefied gas, the system comprising the abovementioned ship, insulated pipelines arranged so as to link the tank installed in the hull of the ship to a floating or onshore storage installation and a pump for driving a liquefied gas through the insulated pipelines from or to the floating or onshore storage installation to or from the tank of the ship.

According to one embodiment, the invention also provides a method for loading or offloading such a ship, wherein a liquefied gas is conveyed through insulated pipelines from or to a floating or onshore storage installation to or from the tank of the ship.

BRIEF DESCRIPTION OF THE FIGURES

The invention will be better understood, and other aims, details, features and advantages thereof will become more clearly apparent from the following description of several particular embodiments of the invention, given purely in an illustrative and nonlimiting manner, with reference to the attached drawings.

FIG. 1 represents a cutaway perspective view of a sealed and thermally insulating tank with membrane according to an embodiment.

FIG. 2 is a partial and cross-sectional schematic view of a portion of the tank of FIG. 1.

FIG. 3 is a cross-sectional view of an intermediate space of the tank of FIG. 1.

FIG. 4 is a cutaway view of a self-supporting tank according to another embodiment.

FIG. 5 is a cutaway schematic representation of a tank of a ship and of a terminal for loading/offloading this tank.

FIG. 6 illustrates a log/log scale diagram indicating the trends of saturating vapour pressures of several chemical species as a function of temperature.

DESCRIPTION OF THE EMBODIMENTS

In relation to FIG. 1, a sealed and thermally insulating tank 1 can be seen that is intended to receive a liquefied gas, for example liquid hydrogen. The tank 1 rests on a bearing structure formed by the inner hull (not represented) of a ship with double-hull (not represented). The tank 1 has a generally polyhedral or prismatic form. The tank 1 has a first transverse wall 2 and a second transverse wall 3, here of octagonal form. In FIG. 1, the first transverse wall 2 is represented only partially in order to allow a view of the internal space of the tank 1. The tank 1 also comprises a ceiling wall 4, a bottom wall 5, bottom chamfer walls 6, lateral walls 7 and top chamfer walls 8. The ceiling wall 4, the bottom wall 5, the bottom chamfer walls 6, the lateral walls 7 and the top chamfer walls 8 extend in the longitudinal direction of the ship, link the first and second transverse walls 2, 3 at transverse edges 9, and meet at longitudinal edges 10.

The sealed and thermally insulating tank 1 comprises, from the outside to the inside of the tank 1, in relation to FIG. 2:

- an outer sealed wall 11,
- a secondary thermally insulating barrier 20 which is fixed to the outer sealed wall 11, the secondary thermally insulating barrier 20 comprising blocks of insulating foam,
- a corrugated secondary sealed membrane 24 borne by the thermally insulating barrier 20,
- an intermediate space 30 comprising a gaseous phase and a primary thermally insulating barrier 25 comprising support pillars,
- a primary sealed membrane 26 borne by the primary thermally insulating barrier 25, the primary sealed membrane 26 being intended to be in contact with the liquefied gas contained in the tank 1.

The gaseous phase of the intermediate space 30 is composed of one or more main chemical species, for example composed of carbon dioxide, and possibly one or more residual chemical species.

The or each main chemical species exhibits a saturating vapour pressure at any temperature lower than 126 K lower than the saturating vapour pressure of nitrogen at said temperature lower than 126 K. In other words, the or each chemical species is or are chosen from among species which are situated to the right of $N_2$ as illustrated in the log/log scale diagram of FIG. 6. In log/log scale, the curves of the saturating vapour pressures of the chemical species are almost all identical but offset in temperature. However, beyond 126 K, the curve of equilibrium of the $N_2$ stops and it is no longer possible to compare the saturating vapour pressure difference with other chemical species.

The pressure in the intermediate space 30 is at an absolute pressure lower than the triple point of said or each main chemical species.

The or each residual chemical species is at a partial pressure lower than 0.1 kPa.

In another embodiment, the tank 111 is a self-supporting tank and comprises, from the outside to the inside:

- a bearing structure 12
- an outer sealed wall 110,
- an intermediate space 130 comprising a gaseous phase and a thermally insulating barrier 125,
- an inner sealed wall 126, and
- an internal space 13 intended to contain the liquefied gas, for example liquid hydrogen. As an alternative to the self-supporting tank, the tank can be of the type with inverted membrane, that is to say comprising a rigid inner wall and a flexible membrane at a distance from the rigid inner wall.

Figure 3:
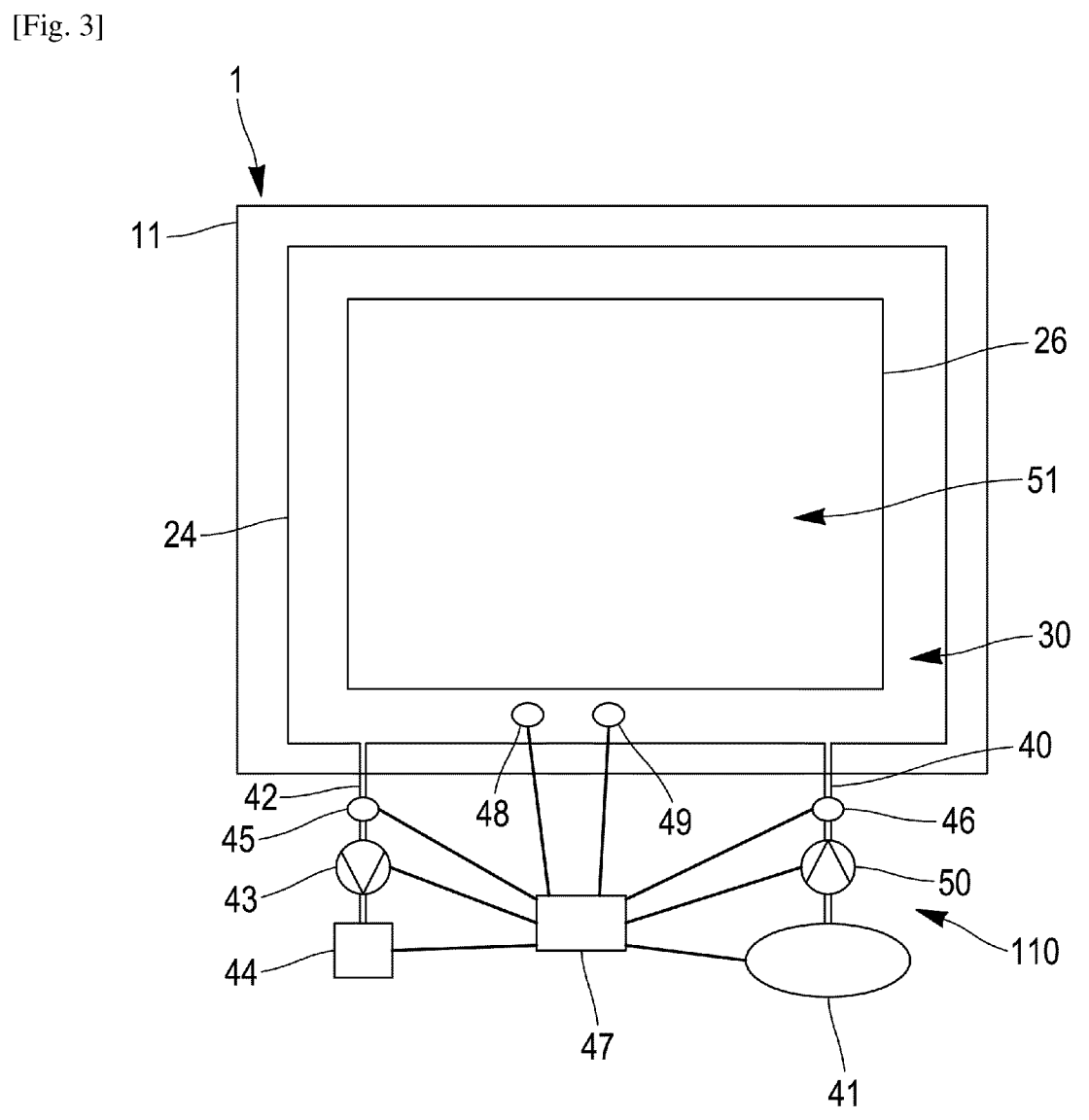

The gaseous phase of the intermediate space 130 illustrated in FIG. 4 can be identical to the gaseous phase of the intermediate space 30 illustrated in FIGS. 2 and 3.

A method for evacuating an intermediate space in a sealed and thermally insulating tank according to an embodiment will be described hereinbelow, in relation to FIG. 3.

The elements that are identical or similar to FIG. 2 bear the same reference numerals.

The method for evacuating an intermediate space in a sealed and thermally insulating tank comprises:

Replacing the gaseous phase present in the intermediate space with a replacement gaseous phase at a temperature higher than 273 K.

The replacement of the gaseous phase is performed via a gas management installation 110 linked to the tank 1.

The gas management installation 110 comprises:

- a supply line 40 linked to a gas source 41 and to a compressor 50 and emerging in the intermediate space 30. The gas source 41 comprises a gas tank filled with one said main species or a gas generator capable of generating one said main species, for example carbon dioxide.
- a suction line 42 linked to a vacuum pump 43 and emerging in the intermediate space 30.

The gas management installation 110 can further comprise different elements making it possible to parameterize and monitor the injection and the suction of gas. For example, the gas management installation 110 comprises one or more devices chosen from among:

- a gas analyzer 44 for analyzing the gas extracted from the secondary space via the suction line 42,
- a gas input 46 and/or gas output 45 flowmeter,
- a control unit 47,
- a pressure sensor 48 situated in the intermediate space 30,
- a temperature sensor 49 situated in the intermediate space 30.

Thus, the gaseous phase is replaced by performing a suction of the gaseous phase from the intermediate space 30 via the suction line 42 during which the vacuum pump 43 is activated, and an injection in which the or each main chemical species is injected in gaseous phase from the gas source 41 to the intermediate space 30.

Optionally, this replacement operation can be performed repeatedly until the gaseous phase exhibits the desired parameters.

In a first example, the gas source is a source of $CO_2$. In a second example, the gas source is a source of trans-1,3,3,3-tetrafluoropropene.

The vacuum pump 43 is then activated in order to lower the pressure to an absolute pressure lower than the triple point of said or each main chemical species.

In a first example, the triple point of carbon dioxide is situated at 519 kPa at 217 K. Thus, for carbon dioxide, the pressure will be lowered to an absolute pressure lower than 519 kPa.

In a second example, the triple point of trans-1,3,3,3-tetrafluoropropene is situated at 0.22 kPa at 168 K. Thus, for trans-1,3,3,3-tetrafluoropropene, the pressure will be lowered to an absolute pressure lower than 0.22 kPa.

Next, the internal space 51 of the tank 1 is filled with liquefied gas, for example liquid hydrogen. Thus, the temperature of the intermediate space will decrease by heat transfer. The temperature of said or each main chemical species of the gaseous phase will decrease and said or each main chemical species will condense directly into solid phase, without passing through the liquid state. This phenomenon will therefore make it possible to further reduce the pressure of the intermediate space.

Such a method described above can be applied similarly to the self-supporting tank 111, illustrated in FIG. 4, and to other tanks having an intermediate space and intended to contain liquefied gas.

A table of comparison of the main chemical species, dinitrogen ($N_2$), carbon dioxide ($CO_2$) and trans-1,3,3,3-tetrafluoropropene (R1234ze(E)), is described below:

TABLE 1

| Species | T triple (K) | P triple (kPa) | Psat at 126 K (kPa) | Psat at 303 K (kPa) | R = Psat($N_2$)/ Psat at 126 K |
|---|---|---|---|---|---|
| $N_2$ | 63 | $1.25 \times 10^1$ | $3.40 \times 10^3$ | N/A (super-critical) | 1 |
| $CO_2$ | 217 | $5.19 \times 10^2$ | $1.40 \times 10^{-2}$ | $7.20 \times 10^3$ | 242857 |
| R1234ze(E) | 168 | $2.20 \times 10^{-1}$ | <0.22 | $5.80 \times 10^2$ | >15455 |

The second column corresponds to the temperature in Kelvin (K) of the triple point of the main species indicated in the lefthand column.

The third column corresponds to the pressure in kilo Pascals (kPa) of the triple point of the main species indicated in the lefthand column.

The fourth and fifth columns correspond to the saturating pressure (Psat), respectively at 126 K and at 303 K, of the main species indicated in the first column on the left.

The sixth column corresponds to the ratio of the saturating pressure of dinitrogen to the saturating pressure of the main chemical species indicated in the lefhand column at 126 K.

Thus, it can be seen that the saturating vapour pressure at any temperature lower than 126 K of the or each main chemical species is lower than the saturating vapour pressure of dinitrogen at the temperature lower than 126 K in a ratio of 242857 for $CO_2$ and of 15455 for R1234ze(E).

Referring to FIG. 5, a cutaway view of a ship 70, for example a hydrogen tanker intended to transport liquefied hydrogen, shows a tank 71, sealed and insulated, of generally prismatic form, mounted in the double-hull 72 of the ship. The wall of the tank 71 comprises a primary sealed barrier intended to be in contact with the liquefied gas, preferentially hydrogen, contained in the tank, a secondary sealed barrier arranged between the primary sealed barrier and the double-hull 72 of the ship, and two insulating barriers arranged respectively between the primary sealed barrier and the secondary sealed barrier and between the secondary sealed barrier and the double-hull 72.

As is known per se, loading/offloading pipelines 73 disposed on the top deck of the ship can be connected, by means of appropriate connectors, to a maritime or port terminal, to transfer a cargo of liquefied gas from or to the tank 71.

FIG. 5 represents an example of maritime terminal comprising a loading and offloading station 75, a submarine line 76 and an onshore installation 77. The loading and offloading station 75 is a fixed offshore installation comprising a movable arm 74 and a riser 78 which supports the movable arm 74. The movable arm 74 bears a bundle of insulated flexible pipes 79 that can be connected to the loading/offloading pipelines 73. The orientable movable arm 74 adapts to all ship templates. A link line that is not represented extends inside the riser 78. The loading and offloading station 75 allows the ship 70 to be loaded and offloaded from or to the onshore installation 77. The latter comprises liquefied gas storage tanks 80 and link lines 81 linked by the submarine line 76 to the loading or offloading station 75. The submarine line 76 allows liquefied gas to be transferred between the loading or offloading station 75 and the onshore installation 77 over a great distance, for example 5 km, which makes it possible to keep the ship 70 at a great distance from the coast during the loading and offloading operations.

To generate the pressure necessary for the transfer of the liquefied gas, pumps embedded in the ship 70 and/or pumps with which the onshore installation 77 is equipped and/or pumps with which the loading and offloading station 75 is equipped are implemented.

Although the invention has been described in relation to several particular embodiments, it is quite clear that it is in no way limited thereto and that it encompasses all the technical equivalents of the means described and the combinations thereof if the latter fall within the context of the invention.

The use of the verb "comprise" or "include" and its conjugate forms does not preclude the presence of elements or steps other than those stated in a claim.

In the claims, any reference symbol between parentheses should not be interpreted as a limitation of the claim.

The invention claimed is:

1. A sealed and thermally insulating tank comprising:

an outer sealed wall, an inner sealed wall (126, 26) situated at a distance from an inner side of the outer sealed wall (11, 110) and defining an internal space (13) intended to contain the liquefied gas, and an intermediate space (30, 130) situated between the outer sealed wall (11, 110) and the inner sealed wall (26, 126), wherein the intermediate space (30, 130) comprises a gaseous phase, the gaseous phase being composed of one or more main chemical species, and one or more residual chemical species, wherein the or each main chemical species exhibits a saturating vapour pressure at any temperature lower than 126 K lower than the saturating vapour pressure of nitrogen at said temperature lower than 126 K, wherein the gaseous phase in the intermediate space (30, 130) is at an absolute pressure lower than a pressure threshold, said pressure threshold being lower than the triple point of said or each main chemical species, and wherein the or each residual chemical species is at a partial pressure lower than 0.1 kPa.

2. The tank according to claim 1, wherein the internal space (13) contains liquefied gas, the liquefied gas having a temperature lower than 273 K.

3. The tank according to claim 2, wherein the internal space (13) contains liquid hydrogen.

4. The tank according to claim 1, wherein said or each main chemical species is chosen from among: carbon dioxide and trans-1,3,3,3-tetrafluoropropene.

5. The tank according to claim 1, wherein carbon dioxide is the single main species of the gaseous phase.

6. The tank according to claim 1, wherein the sealed and thermally insulating tank (1) comprises a secondary sealed membrane (24) situated between the outer sealed wall (11) and the inner sealed wall (26), the intermediate space (30) being formed between the secondary sealed membrane (24) and the inner sealed wall (26), the inner sealed wall (26) being a primary sealed membrane, wherein the intermediate space (30) comprises a primary thermally insulating barrier (25) supporting the primary sealed membrane (26).

7. A method for evacuating an intermediate space in a sealed and thermally insulating tank (1, 111), wherein:

the sealed and thermally insulating tank (1, 111) comprising an outer sealed wall (11, 110), an inner sealed wall (26,126) situated at a distance from an inner side of the outer sealed wall (11, 110) and defining an internal space (13) intended to contain the liquefied gas, and an intermediate space (30, 130) situated between the outer sealed wall (11, 110) and the inner sealed wall (26,126), the method comprising the steps of:

replacing a gaseous phase present in the intermediate space (30, 130) with a replacement gaseous phase at a first temperature, the first temperature being greater than 273 K, the replacement gaseous phase being composed of one or more main chemical species, and one or more residual chemical species, the replacement of the gaseous phase comprising the step of injecting the replacement gaseous phase into the intermediate space (30, 130) at a first pressure, the first pressure in the intermediate space being less than 500 kPa absolute, in which the or each main chemical species is in the gaseous state at the first temperature and at a partial pressure lower than the first pressure, in which the or each main chemical species exhibits a saturating vapour pressure at any temperature lower than 126 K lower than the saturating vapour pressure of nitrogen at said temperature lower than 126 K, the temperature of the internal space (13) being greater than 273 K, then lowering the pressure in the intermediate space (30, 130) to an absolute pressure lower than a pressure threshold, and cooling the sealed and thermally insulating tank (1, 111) by injecting a fluid at a second temperature lower than 273K into the internal space (13) of the sealed and thermally insulating tank (1, 111), wherein the pressure threshold is lower than the triple point of said or each main chemical species, to make said or each main chemical species condense into solid phase upon the cooling of the sealed and thermally insulating tank (1, 111), and wherein the or each residual chemical species is at a partial pressure lower than 0.1 kPa.

8. The method according to claim 7, wherein the first pressure is lower than 110 kPa absolute.

9. The method according to claim 7, wherein the pressure threshold is lower than 1 kPa.

10. The method according to claim 7, wherein said saturating vapour pressure at any temperature lower than 126 K of the or each main chemical species is lower than the saturating vapour pressure of nitrogen at the temperature lower than 126 K in a ratio of less than 1/10.

11. The method according to claim 7, wherein the or each residual chemical species is at a partial pressure lower than 10 Pa.

12. The method according to claim 7, wherein said or each main chemical species is chosen from among: carbon dioxide and trans-1,3,3,3-tetrafluoropropene.

13. The method according to claim 12, wherein the replaced gaseous phase comprises carbon dioxide as single main species.

14. The method according to claim 7, wherein the replacement of the gaseous phase present in the intermediate space (30, 130) comprises:

sucking said gaseous phase present in the intermediate space (30, 130) to the outside of the outer sealed wall (11, 110) until the absolute pressure in the intermediate space (30, 130) is lower than a second pressure threshold, wherein the second pressure threshold is lower than 20 kPa, then injecting the replacement gaseous phase into the intermediate space (30, 130).

15. The method according to claim 14, wherein the steps of suction of the gaseous phase present in the intermediate space (30, 130) and of injection of the replacement gaseous phase are performed repeatedly.

16. The method according to claim 7, wherein the replacement of the gaseous phase present in the intermediate space (30, 130) comprises simultaneously sucking said gaseous phase present in the intermediate space (30, 130) to the outside of the outer sealed wall (11, 110) and injecting the replacement gaseous phase into the intermediate space (30, 130), in order to perform a scavenging of the intermediate space (30, 130) with the replacement gaseous phase.

17. The method according to claim 7, wherein the first temperature is higher than 330 K.

18. The method according to claim 7, wherein the cooling of the sealed and thermally insulating tank (1, 111) is performed by spraying fluid into the internal space of the sealed and thermally insulating tank (1, 111).

19. The method according to claim 7, wherein the cooling of the sealed and thermally insulating tank (1, 111) is performed by filling the internal space (13) of the sealed and thermally insulating tank (1, 111) via a filling line emerging in the bottom part of the sealed and thermally insulating tank (1, 111).

20. The method according to claim 7, wherein the fluid is liquid hydrogen.

21. The method according to claim 7, wherein the sealed and thermally insulating tank (1) comprises a secondary sealed membrane situated between the outer sealed wall and the inner sealed wall, the intermediate space being formed between the secondary sealed membrane and the inner sealed wall, the inner sealed wall being a primary sealed membrane, wherein the intermediate space comprises a primary thermally insulating barrier supporting the primary sealed membrane.

22. The method according to claim 7, wherein the pressure threshold is lower than 0.1 kPa.

23. The method according to claim 7, wherein said saturating vapour pressure at any temperature lower than 126 K of the or each main chemical species is lower than the saturating vapour pressure of nitrogen at the temperature lower than 126 K in a ratio of less than 1/1000.

24. The method according to claim 7, wherein said saturating vapour pressure at any temperature lower than 126 K of the or each main chemical species is lower than the saturating vapour pressure of nitrogen at the temperature lower than 126 K in a ratio of less than 1/10000.

25. The method according to claim 7, wherein the or each residual chemical species is at a partial pressure lower than 1 Pa.

26. The method according to claim 7, wherein the replacement of the gaseous phase present in the intermediate space (30, 130) comprises:

sucking said gaseous phase present in the intermediate space (30, 130) to the outside of the outer sealed wall (11, 110) until the absolute pressure in the intermediate space (30, 130) is lower than a second pressure threshold, wherein the second pressure threshold is lower than 10 kPa, then injecting the replacement gaseous phase into the intermediate space (30, 130).

27. The method according to claim 7, wherein the replacement of the gaseous phase present in the intermediate space (30, 130) comprises:

sucking said gaseous phase present in the intermediate space (30, 130) to the outside of the outer sealed wall (11, 110) until the absolute pressure in the intermediate space (30, 130) is lower than a second pressure threshold, wherein the second pressure threshold is lower than 1 kPa, then injecting the replacement gaseous phase into the intermediate space (30, 130).

28. The method according to claim 7, wherein the first temperature is higher than 373.15 K.

* * * * *